United States Patent [19]

Himmler et al.

[11] Patent Number: 5,194,636
[45] Date of Patent: Mar. 16, 1993

[54] PREPARATION OF BENZYL KETONES AND AN OXIRANE

[75] Inventors: Thomas Himmler, Cologne; Udo Kraatz, Leverkusen; Wolfgang Krämer, Bruscheid; Klaus Stroech, Solingen, all of Fed. Rep. of Germany

[73] Assignee: Bayer Aktiengesellschaft, Leverkusen, Fed. Rep. of Germany

[21] Appl. No.: 845,072

[22] Filed: Mar. 3, 1992

Related U.S. Application Data

[62] Division of Ser. No. 709,679, Jun. 3, 1991, Pat. No. 5,146,001.

[30] Foreign Application Priority Data

Jun. 13, 1990 [DE] Fed. Rep. of Germany ....... 4018926
Sep. 22, 1990 [DE] Fed. Rep. of Germany ....... 4030061

[51] Int. Cl.$^5$ ................ C07D 301/02; C07D 303/08
[52] U.S. Cl. ................ 549/519; 568/323; 568/325
[58] Field of Search ........................... 549/519

[56] References Cited

U.S. PATENT DOCUMENTS

| | | | |
|---|---|---|---|
| 2,845,462 | 7/1958 | Oroshnik | 260/665 G |
| 2,855,397 | 10/1958 | Ramsden | 568/323 |
| 3,080,324 | 3/1963 | Richards et al. | 260/665 G |
| 4,137,324 | 1/1979 | Elliott et al. | 549/519 |
| 4,483,862 | 11/1984 | Richardson et al. | 260/665 G |
| 4,632,999 | 12/1986 | Zerbes et al. | 549/519 |
| 4,886,892 | 12/1989 | Zerbes et al. | 549/519 |
| 4,898,954 | 2/1990 | Mohrmann et al. | 549/519 |
| 4,929,735 | 5/1990 | Reiser et al. | 549/519 |
| 4,960,911 | 10/1990 | Zerber et al. | 549/519 |
| 4,988,829 | 1/1991 | Fiedler et al. | 549/519 |
| 4,992,565 | 2/1991 | Mohrmann et al. | 549/519 |

FOREIGN PATENT DOCUMENTS

| | | | |
|---|---|---|---|
| 94726 | 11/1983 | European Pat. Off. | 549/519 |
| 415320 | 3/1991 | European Pat. Off. | 549/519 |

OTHER PUBLICATIONS

J. Org. Chem., vol. 44, No. 10, 1979, 1613-1618.
J. Org. Chem, 1984, vol. 49, No. 12, 2288-2289.
"Palladium-Catalyzed Acylation of Organozincs and Other Organometallics As a convenient Route to Ketones[1]", pp. 5181-5184 (1983), Tetrahedron Letters, 24.
Chemistry Letters, pp. 1135-1138, 1981. The Chemical Society of Japan.

Primary Examiner—Joseph E. Evans
Attorney, Agent, or Firm—Sprung Horn Kramer & Woods

[57] ABSTRACT

In the preparation of benzyl ketones of the formula

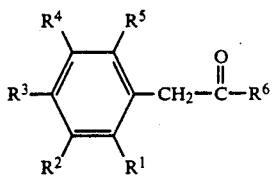
(I)

a benzyl chloride of the formula

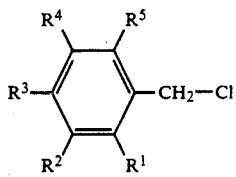
(II)

is reacted with an acid chloride of the formula $R^6$—CO—Cl     (III)

a) in a first stage with an excess of zinc powder in the presence of a diluent at a temperature between 80° C. and 200° C. under an inert gas atmosphere, and separating off the excess zinc powder, thereby to obtain a benzyl derivative of the formula

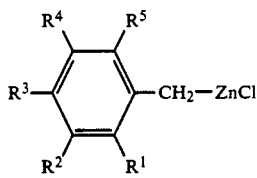
(IV)

and
b) in a second stage reacting the benzyl derivative of the formula (IV) with an acid chloride of the formula (III) in the presence of a palladium catalyst and in the presence of a diluent at a temperature between 0° C. and 150° C. under an inert gas atmosphere.

1 Claim, No Drawings

PREPARATION OF BENZYL KETONES AND AN OXIRANE

This is a division, of application Ser. No. 709,679, filed Jun. 3, 1991, now U.S. Pat. No. 5,146,001.

The present invention relates to a new process for the preparation of benzyl ketones, some of which are known and which can be used as intermediate products for the synthesis of active compounds having fungicidal properties.

The present invention also relates to a new process for the preparation of 2-(2-chlorobenzyl)-2-(1-chlorocyclopropyl)-oxirane, which can likewise be used as an intermediate product for the preparation of active compounds having fungicidal properties.

It is already known that ketones can be prepared by reaction of organic acid halides with organometallic compounds. Possible organometallic components here are compounds which are derived from magnesium, cadmium, copper, manganese, mercury, aluminum, rhodium, boron or silicon. A disadvantage of this manufacturing method is, however, that undesirable side reactions proceed. An addition of the organometallic compound onto the ketone formed thus occurs in many cases. As a result of this, the yield of ketone is reduced drastically. The fact that, for example, organometallic compounds of mercury or cadmium are highly toxic and that, for example, organo-metallic compounds of rhodium are very expensive is also a disadvantage. Another disadvantage is that in most cases the organometallic compounds required can be prepared only via other organometallic substances, such as, for example, Grignard compounds or organolithium compounds. The variation in the radicals to be introduced is thus greatly restricted.

It is furthermore already known that ketones are producible by palladiua-catalyzed coupling of organic acid chlorides with organotin compounds [compare J. Org. Chem. 44, (1979) 1613]. One disadvantage of this method is to be seen in the fact that the organotin compounds are also prepared via other organometallic intermediate stages. The synthesis of the ketones within short reaction times furthermore is only possible by this method if hexamethyl-phosphoric acid triamide is used as the diluent.

The synthesis of ketones from organic acid chlorides and organozinc compounds in the presence of palladium catalysts has moreover been described in the literature compare J. Org. Chem. 49, (1984) 2288 and Tetrahedron Letters 1983, 5181–5184]. A disadvantage of this method is that here also the organozinc compounds are prepared with the aid of Grignard reagents. The nature of the substituents to be introduced is thus essentially limited to unsubstituted aryl and alkyl radicals. Ethers or mixtures of ethers with other solvents, which can be handled industrially only with difficulty, are furthermore required as diluents for carrying out the reaction.

It is moreover already known that benzyl ketones can be prepared by palladium-catalyzed coupling of benzyl bromides with organic acid chlorides in the presence of zinc powder (compare Chem. Lett. 1981. 1135 to 1138). However, this process is also associated with some disadvantages. Thus, relatively large amounts of palladium catalysts must be used. The desired products are furthermore obtained only in relatively low yields if chlorides of branched aliphatic acids are employed. Finally, it is also already known that benzyl phenyl ketone is producible by palladium-catalyzed coupling of benzoyl chloride with benzyl chloride in the presence of zinc powder (compare Chem. Lett. 1981. 1136). Nevertheless, the compound in question is obtained in only a very low yield.

It is furthermore known that ketones can be converted into oxiranes with the aid of trimethylsulphonium salts in the presence of bases (compare Ber. 96, 1881–1890 (1963), J. Amer. Chem. Soc. 87. 1353–1364 (1965), DE-OS (German Published Specification) 3,315,619, DE-OS (German Published Specification) 3,315,524, DE-OS (German Published Specification) 3,315,510 and DE-OS (German Published Specification) 3,315,681). However, it is a disadvantage that the yields vary greatly according to the particular sulphonium salt used, the diluent and the base.

It is moreover known that certain oxiranes can be prepared by treating the corresponding chlorohydrins with bases (compare EP-OS (European Published Specification) 0,297,345). Although this process gives the desired substances in good yields, the synthesis of the starting substances required is however relatively expensive.

It has now been found that benzyl ketones of the formula

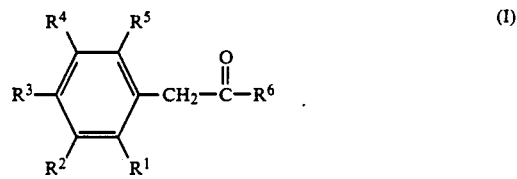

(I)

in which

R¹, R², R³, R⁴ and R⁵ independently of one another represent hydrogen, halogen, alkyl having 1 to 6 carbon atoms, halogenoalkyl having 1 to 6 carbon atoms and 1 to 13 halogen atoms, alkoxy having 1 to 6 carbon atoms, halogenoalkoxy having 1 to 6 carbon atoms and 1 to 13 halogen atoms, cyano or optionally halogensubstituted phenoxy, or represent aryl having 6 to 10 carbon atoms, it being possible for each of the aryl radicals to be substituted by halogen, alkyl having 1 to 4 carbon atoms, halogenoalkyl having 1 to 4 carbon atoms and 1 to 5 halogen atoms, alkoxy having 1 to 4 carbon atoms and/or halogenoalkoxy having 1 to 4 carbon atoms and 1 to 5 halogen atoms, or R¹, R², R³, R⁴ and R⁵ independently of one another represent a radical of the formula

—COOR.

wherein

R⁷ represents alkyl having 1 to 6 carbon atoms, phenyl or benzyl, and

R⁶ represents alkyl having 1 to 18 carbon atoms, halogenoalkyl having 1 to 18 carbon atoms and 1 to 12 halogen atoms, alkenyl having 2 to 18 carbon atoms or halogenoalkenyl having 2 to 18 carbon atoms and 1 to 12 halogen atoms, alkoxycarbonylalkyl with 1 to 6 carbon atoms in the alkyl part and 1 to 6 carbon atoms in the alkoxy part or represents cycloalkyl having 3 to 8 carbon atoms, or represents cycloalkenyl having 5 to 8 carbon atoms, it being possible for each of the cycloalkyl and cycloalkenyl radicals to be substituted by halogen, alkyl having 1 to 4 carbon atoms, halogenoalkyl having 1 to 4 carbon atoms and 1 to 7 halogen atoms, alkoxy having 1 to 4 carbon atoms, halogenolkoxy having 1 to 4 carbon atoms and 1 to 7 halogen atoms, alkenyl having 2 to 6 carbon atoms and/or phenyl which is optionally substituted by halogen and/or alkyl having 1 to 4 carbon atoms, or $R^6$ represents alkyl having 6 to 10 carbon atoms, or represents alkyl having 6 to 10 carbon atoms in the aryl part and 1 to 4 carbon atoms in the alkyl pat, or represents aralkenyl having 6 to 10 carbon atoms in the aryl part and 2 to 4 carbon atoms in the alkenyl part, or represents aroxyalkyl having 6 to 10 carbon atoms in the aryl part and 1 to 4 carbon atoms in the alkyl part, it being possible for each of these radicals to be substituted in the aryl part by halogen, alkyl having 1 to 6 carbon atoms, halogenoalkyl having 1 to 4 carbon atoms and 1 to 5 halogen atoms, alkoxy having 1 to 4 carbon atoms and/or halogenoalkoxy having 1 to 4 carbon atoms and 1 to 5 halogen atoms, or $R^6$ represents a heteroaromatic radical which has 5 or 6 ring members and 1 or 2 heteroatoms and is optionally substituted by halogen and/or alkyl having 1 to 4 carbon atoms, or $R^6$ represents a radical of the formula

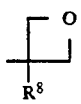

wherein $R^6$ represents alkyl having 1 to 4 carbon atoms, or represents halogen, are obtained by reaction of benzyl chlorides of the formula

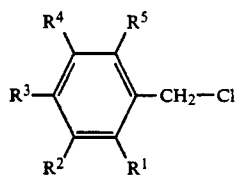

(II)

in which $R^1$, $R^2$, $R^3$, $R^4$ and $R^5$ have the abovementioned meanings, with acid chlorides of the formula

$R^6$—CO—Cl    (III)

in which $R^6$ has the abovementioned meaning, in the presence of zinc powder and a palladium catalyst and in the presence of a diluent, by a process in which a) in a first stage a benzyl chloride of the formula (II) is reacted with an excess of zinc powder in the presence of a diluent at temperatures between 30° C. and 200° C. under an inert gas atmosphere, the excess zinc powder is separated off and then b) in a second stage the benzyl derivative formed, of the formula

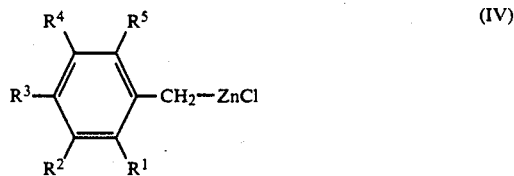

in which $R^1$, $R^2$, $R^3$, $R^4$ and $R^5$ have the abovementioned meanings, is reacted with an acid chloride of the formula (III) in the presence of a palladium catalyst and in the presence of a diluent at temperatures between 0° C and 150° C under an inert gas atmosphere.

It is to be regarded as exceptionally surprising that benzyl ketones of the formula (I) can be prepared in a considerably higher yield by the two-stage process according to the invention than by the corresponding process which is already known, in which the reaction is carried out in a single stage. The result is above all also unexpected because on the basis of the known prior art it was to be assumed that benzyl bromides react more easily than benzyl chlorides under the process conditions.

The process according to the invention is distinguished by a number of advantages. The use of only a very small amount of palladium catalyst is thus necessary. The ketones desired are furthermore obtained in high yields. It is moreover advantageous that the process is widely applicable in respect of the substituents in the benzyl part and in respect of the acid radical.

If 2-chlorobenzyl chloride is used as the starting substance and 1-chloro-cyclopropane-carbonyl chloride is used as the reaction component, the course of the process according to the invention can be illustrated by the following equation:

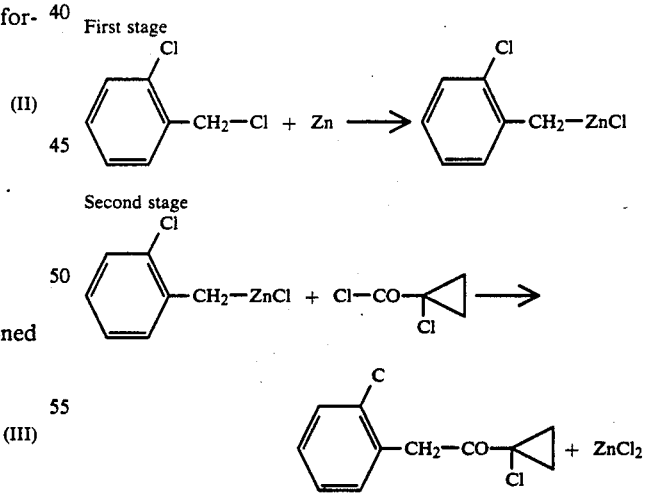

Formula (II) provides a general definition of the benzyl chlorides required as starting substances in carrying out the process according to the invention for the preparation of benzyl ketones. In this formula, the substituents $R^1$, $R^2$, $R^3$, $R^4$ and $R^5$ have the abovementioned meanings. Benzyl chlorides of the formula (II) in which $R^1$, $R^2$, $R^3$, $R^4$ and $R^5$ independently of one another represent hydrogen, fluorine, chlorine, bromine, alkyl having 1 to 4 carbon atoms, halogenoalkyl having 1 to 4 carbon atoms and 1 to 5 fluorine and/or chlorine atoms, alkoxy having 1 to 4 carbon atoms, halogenoalkoxy having 1 to 4 carbon atoms and 1 to 5 fluorine and/or chlorine atoms, cyano or phenoxy which is optionally substituted by 1 to 3 fluorine and/or chlorine atoms, or represent phenyl or naphthyl, it being possible for each of the last two radicals mentioned to be substituted by one to three identical or different substituents from the group comprising fluorine, chlorine, alkyl having 1 to 3 carbon atoms, halogenoalkyl having 1 or 2 carbon atoms and 1 to 5 fluorine and/or chlorine atoms, alkoxy having 1 to 3 carbon atoms or halogenoalkoxy having 1 or 2 carbon atoms and 1 to 5 fluorine and/or chlorine atoms, or $R^1$, $R^2$, $R^3$, $R^4$ and $R^5$ independently of one another represent a radical of the formula

—COOR$^7$ wherein $R^7$ represents alkyl having 1 to 4 carbon atoms, phenyl or benzyl
can preferably be used.

Benzyl chlorides which can particularly preferably be used are those of the formula (II) in which $R^1$ represents hydrogen, fluorine, chlorine, bromine, methyl, ethyl, trifluoromethyl, trichloromethyl, methoxy, ethoxy, trifluoromethoxy, trichloromethoxy, cyano, phenoxy which is optionally substituted by one or two fluorine and/or chlorine atoms, or phenyl which is optionally substituted by one or two identical or different substituents from the group comprising fluorine, chlorine, methyl, ethyl, trifluoromethyl, trichloromethyl, methoxy, ethoxy, trifluoromethoxy or trichloromethoxy, or represents the radical of the formula

—COOR$^7$ wherein $R^7$ represents methyl, ethyl, phenyl or benzyl, $R^2$ represents hydrogen, fluorine, chlorine, bromine, methyl, ethyl, trifluoromethyl, trichloromethyl, methoxy, ethoxy, trifluoromethoxy, trichloromethoxy, cyano, phenoxy which is optionally substituted by one or two fluorine and/or chlorine atoms, or phenyl which is optionally substituted by one or two identical or different substituents from the group comprising fluorine, chlorine, methyl, ethyl, trifluoromethyl, trichloromethyl, methoxy, ethoxy, trifluoromethoxy or trichloromethoxy, or represents the radical of the formula

—COOR$^7$ wherein $R^7$ represents methyl, ethyl, phenyl or benzyl, $R^3$ represents hydrogen, fluorine, chlorine, bromine, methyl, ethyl, trifluoromethyl, trichloromethyl, methoxy, ethoxy, trifluoromethoxy, trichloromethoxy, cyano, phenoxy which is optionally substituted by one or two fluorine and/or chlorine atoms, or phenyl which is optionally substituted by one or two identical or different substituents from the group comprising fluorine, chlorine, methyl, ethyl, trifluoromethyl, trichloromethyl, methoxy, ethoxy, trifluoromethoxy or trichloromethoxy, or represents the radical of the formula

—COOR$^7$ wherein $R^7$ represents methyl, ethyl, phenyl or benzyl, $R^4$ represents hydrogen, fluorine, chlorine, bromine, methyl, ethyl, trifluoromethyl, trichloromethyl, methoxy, ethoxy, trifluoromethoxy, trichloromethoxy, cyano, phenoxy which is optionally substituted by one or two fluorine and/or chlorine atoms, or phenyl which is optionally substituted by one or two identical or different substituents from the group comprising fluorine, chlorine, methyl, ethyl, trifluoromethyl, trichloromethyl, methoxy, ethoxy, trifluoromethoxy or trichloromethoxy, or represents the radical of the formula

—COOR$^7$ wherein $R^7$ represents methyl, ethyl, phenyl or benzyl, and $R^5$ represents hydrogen, fluorine, chlorine, bromine, methyl, ethyl, trifluoromethyl, trichloromethyl, methoxy, ethoxy, trifluoromethoxy, trichloromethoxy, cyano, phenoxy which is optionally substituted by one or two fluorine and/or chlorine atoms, or phenyl which is optionally substituted by one or two identical or different substituents from the group comprising fluorine, chlorine, methyl, ethyl, trifluoromethyl, trichloromethyl, methoxy, ethoxy, trifluoromethoxy or trichloromethoxy, or represents the radical of the formula

—COOR$^7$ wherein $R^7$ represents methyl, ethyl, phenyl or benzyl.

The benzyl chlorides of the formula (II) are known or can be prepared in a simple manner by processes which are known in principle.

Formula (III) provides a general definition of the acid chlorides required as reaction components in carrying out the process according to the invention for the preparation of benzyl ketones. In this formula, the radical $R^6$ has the abovementioned meanings. Acid chlorides of the formula (III) which can preferably be used are those in which $R^6$ represents alkyl having 1 to 6 carbon atoms, halogenoalkyl having 1 to 6 carbon atoms and 1 to 6 fluorine, chlorine and/or bromine atoms, alkenyl having 2 to 8 carbon atoms or halogenoalkenyl having 2 to 8 carbon atoms and 1 to 6 fluorine, chlorine and/or bromine atoms, alkoxycarbonylalkyl with 1 to 4 carbon atoms in the alkyl part and 1 to 4 carbon atoms in the alkoxy part, or represents cycloalkyl having 3 to 7 carbon atoms, or represents cycloalkenyl having 5 to 7 carbon atoms, it being possible for the cycloalkyl and cycloalkenyl radicals to be substituted by one to eight identical or different substituents from the group comprising fluorine, chlorine, bromine, alkyl having 1 to 3 carbon atoms, halogenoalkyl having 1 to 3 carbon atoms and 1 to 5 fluorine and/or chlorine atoms, alkoxy having 1 to 3 carbon atoms, halogenoalkoxy having 1 to 3 carbon atoms and 1 to 5 fluorine and/or chlorine atoms, by alkenyl having 2 to 4 carbon atoms and/or phenyl which is optionally substituted by one or two identical or different substituents from the group comprising fluorine, chlorine, methyl and/or ethyl, or $R^6$ represents phenyl, naphthyl, phenylalkyl having 1 to 4 carbon atoms in the alkyl part, phenylalkenyl having 2 or 3 carbon atoms in the alkenyl part, or phenoxyalkyl having to 4 carbon atoms in the alkyl part, it being possible for each of these previously mentioned radicals to be substituted in the aryl part by one to three identical or different substituents from the group comprising fluorine, chlorine, bromine, alkyl having 1 to 3 carbon atoms, halogenoalkyl having 1 to 3 carbon atoms and 1 to 5 fluorine and/or chlorine atoms, alkoxy having 1 to 3 carbon atoms and/or halogenoalkoxy having 1 to 3 carbon atoms and 1 to 5 fluorine and/or chlorine atoms, or $R^6$ represents a heteroaromatic radical which has 5 or 6 ring members and 1 or 2 nitrogen, oxygen and/or sulphur atoms and is optionally substituted by one or two identical or different substituents from the group comprising fluorine, chlorine, bromine, methyl and/or ethyl, or $R^6$ represents a radical of the formula

wherein
$R^8$ represents methyl, ethyl, fluorine, chlorine or bromine.

Acid chlorides of the formula (III) which can particularly preferably be used are those in which $R^6$ represents alkyl having 1 to 4 carbon atoms, halogenoalkyl having 1 to 4 carbon atoms and 1 to 5 fluorine, chlorine and/or bromine atoms, alkenyl having 2 to 6 carbon atoms or halogenoalkenyl having 2 to 6 carbon atoms and 1 to 5 fluorine, chlorine and/or bromine atoms, alkoxycarbonylalkyl having 1 to 3 carbon atoms in the alkyl part and 1 to 3 carbon atoms in the alkoxy part, or represents cycloalkyl having 3 to 7 carbon atoms or cycloalkenyl having 5 to 7 carbon atoms, it being possible for the cycloalkyl and cycloalkenyl radicals to be substituted by one to eight identical or different substituents from the group comprising fluorine, chlorine, bromine, methyl, ethyl, propyl, trifluoromethyl, trichloromethyl, methoxy, ethoxy, trifluoromethoxy, trichloromethoxy, alkenyl having 2 or 3 carbon atoms and/or phenyl which is optionally substituted by one or two identical or different substituents from the group comprising fluorine, chlorine, methyl and/or ethyl, or $R^6$ represents phenyl, naphthyl, phenylalkyl having 1 or 2 carbon atoms in the alkyl part, phenylakenyl having 2 carbon atoms in the alkenyl part or phenoxyalkyl having 1 to 3 carbon atoms in the alkyl part, it being possible for each of the four abovementioned radicals to be substituted in the aryl part by one to three identical or different substituents from the group comprising fluorine, chlorine, bromine, methyl, ethyl, trifluoromethyl, trichloromethyl, methoxy, ethoxy, trifluoromethoxy and/or trichloromethoxy, or $R^6$ represents pyrrolyl, pyridinyl, pyrimidinyl, furyl or thiophenyl, each of which is optionally substituted by one or two identical or different substituents from the group comprising fluorine, chlorine, bromine, methyl and/or ethyl.

$R^6$ represents a radical of the formula

wherein
$R^8$ represents methyl, ethyl, fluorine, chlorine or bromine.

The acid chlorides of the formula (III) are known or can be prepared in a simple manner by processes which are known in principle.

The zinc powder can be employed in various particle sizes in carrying out the process according to the invention for the preparation of benzyl ketones. Zinc dust or zinc powder of small particle size can preferably be used.

Possible palladium catalysts for carrying out the process according to the invention for the preparation of benzyl ketones are all the customary palladium(II) salts, palladium(II) complexes and palladium(0) complexes. Compounds which can preferably be used are palladium(II) chloride, palladium(II) acetate, bis(triphenylphosphine)palladium(II) chloride, bis(benzonitrile)-palladium(II) chloride and tetrakis(triphenylphosphine)-palladium(0).

All the customary inert organic solvents can be employed as diluents in carrying out the process according to the invention for the preparation of benzyl ketones both in the first and in the second stage. Solvents which can preferably be used are ethers, such as diethyl ether, tert.-butyl methyl ether, tert.-amyl methyl ether, tetrahydrofuran, 2,5-dimethyl-tetrahydrofuran, ethylene glycol dimethyl ether, ethylene glycol tert.-butyl methyl ether, diethylene glycol diethyl ether and dioxane, and furthermore nitriles, such as acetonitrile, and moreover amides, such as dimethylformamide and dimethylacetamide. The solvents are preferably employed in dry form.

Possible inert gases in carrying out the process according to the invention for the preparation of benzyl ketones both in the first and in the second stage are all the customary inert gases. Gases which can preferably be used are helium, argon and nitrogen.

The reaction temperatures can be varied within a substantial range in carrying out the process according to the invention for the preparation of benzyl ketones both in the first and in the second stage. The first stage is in general carried out at temperatures between 30° C. and 200° C., preferably between 50° C. and 150° C. The second stage is in general carried out at temperatures between 0° C. and 150° C., preferably between 20° C. and 100° C.

The reaction times can also be varied within a substantial range in the case of the process according to the invention for the preparation of benzyl ketones in carrying out both the first and the second stage. The reaction times in the first stage are in general between 0.5 and 4 hours, preferably between 1 and 3 hours. The reaction times in the second stage are in general between 0.1 and 5 hours, preferably between 0.5 and 3 hours.

The process according to the invention for the preparation of benzyl ketones is in general carried out under normal pressure. However, it is also possible for the process to be carried out under reduced or increased pressure.

In carrying out the first stage of the process according to the invention for the preparation of benzyl ketones, the benzyl chloride of the formula (II) is reacted with an excess of zinc. In general between 1.05 and 3 moles preferably between 1.1 and 2.5 moles, particularly preferably between 1.25 and 2.0 moles, of zinc are employed per mole of benzyl chloride of the formula (II).

The amount of palladium catalyst can be varied within a certain range in carrying out the second stage or the process according to the invention for the preparation of benzyl ketones. In general between 0.0001 and 1 mole%, preferably between 0.0025 and 0.1 mole %, particularly preferably between 0.005 and 0.05 mole %, of palladium catalyst are employed per mole of acid chloride of the formula (III).

The ratio of benzyl chloride of the formula (II) to acid chloride of the formula (III) can be varied within a substantial range in carrying out the process according to the invention for the preparation of benzyl ketones. In general between 1.01 and 1.25 moles, preferably between 1.05 and 1.2 mole of benzyl chloride of the formula (II) are employed per mole of acid chloride of the formula (III).

When the reaction in the first stage of the process according to the invention for the preparation of benzyl ketones has ended, the excess zinc can be separated off by customary methods. The zinc can be removed, for example, by filtration or centrifugation, or also by pumping off the supernatant solution after the zinc has settled.

In carrying out the process according to the invention for the preparation of benzyl ketones, a procedure is specifically followed in which the benzyl chloride of the formula (II) is first reacted with zinc in a suitable diluent under an inert gas atmosphere, the excess zinc is then separated off, the acid chloride of the formula (III) and the palladium catalyst are added to the solution which remains and the components are allowed to react until the reaction has ended. Working up is by customary methods. In the procedure followed in general, water and if appropriate dilute aqueous mineral acid are added to the reaction mixture, if appropriate after prior filtration and if appropriate after dilution with an organic solvent of low water-miscibility, and the organic phase is separated off, dried and concentrated. The product which remains can be freed from any impurities which it still contains by customary methods, such as, for example, distillation or recrystallization.

The benzyl ketones of the formula (I) which can be prepared by the process according to the invention are known in some cases (compare Chem. Lett. 1981, 1135–1138, EP-OS (European Published Specification) 0,015,756 and U.S. Patent Specification 4,123,542).

The benzyl ketones of the formula (I) are useful intermediate products for the synthesis of active compounds having fungicidal properties. Azolyl derivatives of the formula

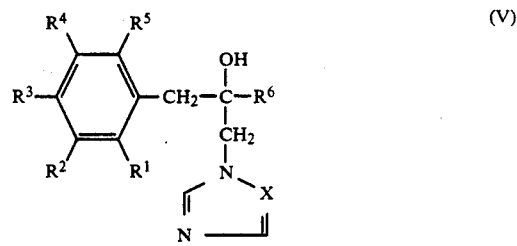
(V)

in which
$R^1$, $R^2$, $R^3$, $R^4$, $R^5$ and $R^6$ have the abovementioned meanings and
X represents nitrogen or a CH group,
can thus be prepared by reacting benzyl ketones of the formula

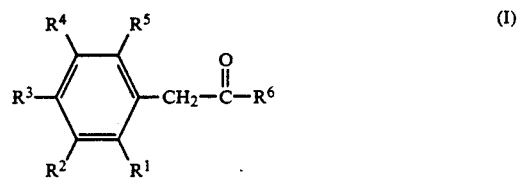
(I)

in which
$R^1$, $R^2$, $R^3$, $R^4$, $R^5$ and $R^6$ have the abovementioned meanings,
either
α) with dimethyloxosulphonium methylide of the formula

(VI)

or
β) with dimethylsulphonium methylide of the formula

(VII)

in the presence of a diluent, such as, for example, tert.-butanol, tetrahydrofuran, dioxane, toluene or dimethyl sulphoxide, at temperatures between 10° C. and 6020 C., and reacting the resulting oxiranes of the formula

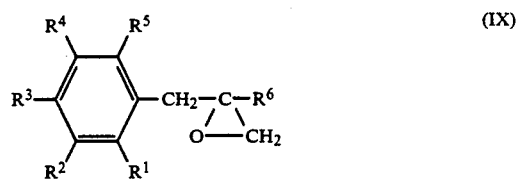
(IX)

in which
$R^1$, $R^2$, $R^3$, $R^4$, $R^5$ and $R^6$ have the abovementioned meanings,
with azoles of the formula

(X)

in which

X has the abovementioned meaning, in the presence of an acid-binding agent and in the presence of a diluent at temperatures between 50° C. and 150° C.

In this connection, it has been found that 2-(2-chlorobenzyl) -2-(1-chloro-cyclopropyl)-oxirane of the formula

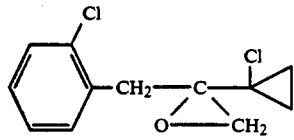
(IX-1)

is obtained by a process in which 2-chlorobenzyl 1-chlorocyclopropyl ketone of the formula

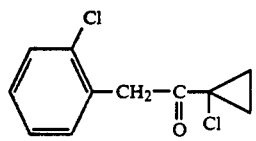
(I-1)

is reacted with trimethylsulphoxonium chloride of the formula

(XI)

either

γ) in the presence of an alcohol and in the presence of an alkali metal hydroxide or an alkali metal alcoholate, or δ) in the presence of toluene or xylene and in the presence of aqueous sodium hydroxide solution or potassium hydroxide solution at temperatures between 10° C. and 60° C.

It is to be considered as being extremely surprising that 2-(2-chlorobenzyl)-2-(1-chloro-cyclopropyl)-oxirane of the formula (IX-1) can be prepared in an extremely high yield by the above process precisely by using trimethylsulphoxonium chloride of the formula (XI), which is not very customary, since when other customary ylide-forming agents are employed, the yields of the desired oxirane are drastically lower.

The process according to the invention for the preparation of 2-(2-chlorobenzyl)-2-(1-chloro-cyclopropyl)oxirane of the formula (IX-1) is distinguished by a number of advantages. Thus, the reaction components required are available in a simple manner and also on an industrial scale. The synthesis procedure and the isolation of the desired substance furthermore presents no problems at all. It is moreover particularly advantageous that the oxirane of the formula (IX-1) is available in an extremely high yield and an excellent purity by this method.

The course of the process according to the invention for the preparation of 2-(2-chlorobenzyl)-2-(1-chloro-cyclopropyl)-oxirane of the formula (IX-1) can be illustrated by the following equation:

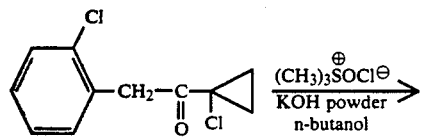

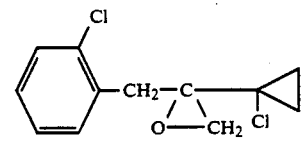

The trimethylsulphoxonium chloride of the formula (XI) required as an ylide-forming agent in the process according to the invention for the preparation of the oxirane of the formula (IX-1) is known (compare Act. Chem. Scand Ser. B. 28, (1974) 590).

The preferred possible diluent in carrying out variant γ of the process according to the invention for the preparation of the oxirane of the formula (IX-1) is n-butanol. Preferred possible bases are sodium hydroxide and potassium hydroxide in solid form. They can be employed as pellets, flakes or powder. Sodium methylate, sodium ethylate and sodium butanolate are furthermore also preferred possible bases.

Variant δ of the process according to the invention for the preparation of the oxirane of the formula (IX-1) is preferably carried out in a two-phase system. Possible diluents are toluene and xylene; bases which can be employed are aqueous sodium hydroxide solution or potassium hydroxide solution.

The reaction temperatures can be varied within a certain range in carrying out the process according to the invention for the preparation of the oxirane of the formula (IX-1) both in variant γ and in variant δ. The reaction is in general carried out at temperatures between 10° C. and 60° C., preferably between 20° C. and 50° C.

The process according to the invention for the preparation of the oxirane of the formula (IX-1) is in general carried out under normal pressure both in variant γ and in variant δ. However, it is also possible for the reaction to be carried out under increased or reduced pressure.

In carrying out the process according to the invention for the preparation of the oxirane of the formula (IX-1) by variant γ, in general 1 to 3 moles, preferably 1 to 2 moles of trimethylsulphoxonium chloride of the formula (XI) and 1 to 3 moles, preferably 1 to 2moles, of base are employed per mole of 2-chlorobenzyl 1-chlorocyclopropyl ketone of the formula (I-1). In carrying out the process by variant δ, in general 1 to 3 moles, preferably 1 to 2 moles, of trimethylsulphoxonium chloride of the formula (XI) and 1 to 3 moles, preferably 1 to 2 moles, of base are employed per mole of 2-chlorobenzyl 1-chloro-cyclopropyl ketone of the formula (I-1). Working up is in each case carried out by customary methods. A procedure is in general followed in which water is added to the reaction mixture when the reaction has ended, the organic phase is separated off, washed with water if appropriate and concentrated, and if appropriate the residue which remains is distilled.

The procedure for the processes according to the invention is illustrated by the following examples.

EXAMPLE 1

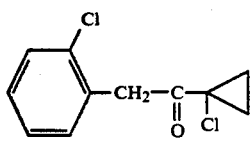 (I-1)

A mixture of 32.4 g (0.5 mol) of zinc powder, 53.1 g (0.33 mol) of 2-chlorobenzyl chloride and 375 ml of dry ethylene glycol dimethyl ether is heated under reflux under a nitrogen atmosphere for 2 hours. The reaction mixture is then filtered under nitrogen. 41.7 g (0.3 mol) of 1-chlorocyclopropane-carbonyl chloride and 21 mg (0.01 mol %) of bis(triphenylphosphine)-palladium(II) chloride are added to the filtrate and the mixture is heated under reflux under a nitrogen atmosphere for 2 hours. After cooling to room temperature, the reaction mixture is filtered and the filtrate is concentrated under reduced pressure. The residue is taken up in toluene, the mixture is extracted by shaking with dilute aqueous hydrochloric acid, the organic phase is dried and the solvent is stripped off under reduced pressure. The residue which remains is subjected to fractional distillation. 57.2 g of an oil which, according to the gas chromatogram, consists to the extent of 95% of 2-chlorobenzyl 1-chloro-cyclopropyl ketone are obtained. The yield is accordingly calculated as 79% of theory.

EXAMPLE 2

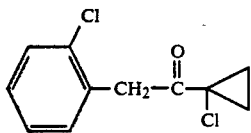 (I-1)

A mixture of 2.6 g (40 mmol) of zinc dust (particle size 325 mesh), 3.2 g (20 mmol) of 2-chlorobenzyl chloride and 25 ml of dry tetrahydrofuran is heated under reflux under a nitrogen atmosphere for 1.5 hours. After the reaction mixture has been cooled to room temperature, it is filtered under nitrogen. 2.8 g (20 mmol) of 1-chlorocyclopropane-carbonyl chloride and 7.3 mg (0.05 mol %) of bis(triphenylphosphine)-palladium(II) chloride are added to the filtrate and the mixture is heated under reflux under a nitrogen atmosphere for 2 hours. It is ascertained by analysis by gas chromatography that 2-chlorobenzyl 1-chlorocyclopropyl ketone is formed in a yield of 85% of theory.

EXAMPLE 3

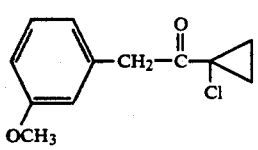 (I-2)

A mixture of 3.9 g (60 mmol) of zinc powder, 4.7 g (30 mmol) of 3-methoxy-benzyl chloride and 45 ml of dry ethylene glycol dimethyl ether is heated under reflux under a nitrogen atmosphere for 3 hours. The reaction mixture is then filtered under nitrogen. 3.5 g (25 mmol) of 1-chlorocyclopropane-carbonyl chloride and 17.5 mg (0.1 mol %) of bis(triphenylphosphine)-palladium(II) chloride are added to the filtrate and the mixture is heated under reflux under a nitrogen atmosphere for hour. It is ascertained by analysis by gas chromatography that 3-methoxybenzyl 1-chlorocyclopropyl ketone has formed in a yield of 59% of theory.

EXAMPLE 4

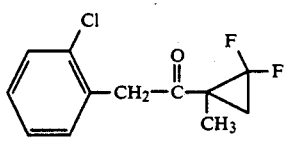 (I-3)

A mixture of 6.5 g (100 mmol) of zinc powder, 10.6 g (66 mmol) of 2-chlorobenzyl chloride and 75 ml of dry ethylene glycol dimethyl ether is heated under reflux under a nitrogen atmosphere for 1 hour. The reaction mixture is then filtered under nitrogen. 6.9 g (44.6 mmol) of 2,2-difluoro-1-methyl-cyclopropanecarbonyl chloride and 21 mg (0.07 mol %) of bis(triphenylphosphine)-palladium(II) chloride are added the filtrate and the mixture is heated under reflux under a nitrogen atmosphere for 1.5 hours. The reaction mixture is then filtered under nitrogen. The filtrate is diluted with toluene and extracted by shaking successively with dilute aqueous hydrochloric acid and water, and the organic phase is dried and concentrated by stripping off the solvent under reduced pressure. The residue which remains is subjected to distillation. 8.0 g (73% of theory) of 2-chlorobenzyl (2,2-difluoro-1-methyl)-cyclopropyl ketone are obtained in this manner in the form of an oil.

$^1$H-NMR(200 MHz, CDCl$_3$) : δ=1.2–1.4(m;1H), 1.6(m;3H), 2.25–2.45(m;1H), 3.9(d,J≈18 Hz;1H) 7.1–7.45(m;4H) ppm.

The benzyl ketones listed in the following examples are also prepared by the methods described above.

EXAMPLE 5

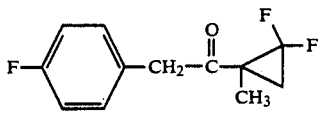 (I-4)

Yield: 85% of theory.

$^1$H-NMR(200 MHz,CDCl$_3$): δ=1.2–1.35(m;1H), 1.5–1.6(m;3H), 2.25–2.4(m;1H), 3.8(d,J≈17 Hz;1H), 3.84 (d,J≈17 Hz;1H), 6.9–7.2(m;4H) ppm.

EXAMPLE 6

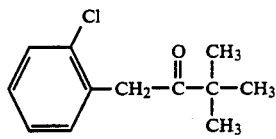 (I-5)

Yield: 74% of theory,

EXAMPLE 7

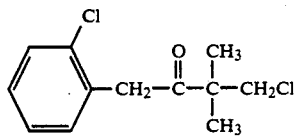 (I-6)

Yield: 60% of theory.
¹H-NMR (200 MHz, CDCl₃): δ=1.34(s;6H), 3.65(s;2H), 3.98(s;2H), 7.2-7.5(m;4H) ppm.

EXAMPLE 8

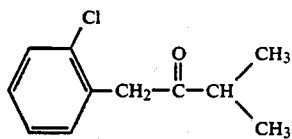
(I-7)

Yield: 91% of theory.
¹H-NMR (200 HMz, CDCl₃) : δ1.13(s;3H), 1.18(s;3H), 2.6-2.8(m;1H), 3.9(s;2H), 7.1-7.4(m;4H) ppm.

EXAMPLE 9

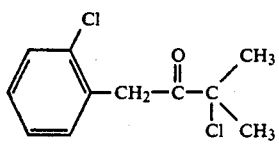
(I-8)

Yield: 85% of theory.
¹H-NMR (200 MHz, CDCl₃) : δ=1.78(s;6H), 4.25(s;2H), 7.1-7.4(m;4H) ppm.

EXAMPLE 10

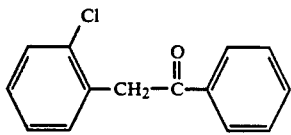
(I-9)

Yield: 66% of theory.
Melting point: 70° C.

EXAMPLE 11

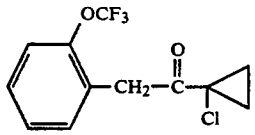
(I-10)

Yield: 82% of theory. ¹H-NMR (200 MHz, CDCl₃) : δ=1.3-1.43(m;2H), 1.63-1.73 (m;2H), 4.21(s;2H), 7.1-7.3(m;4H) ppm.

EXAMPLE 12

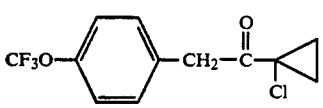
(I-11)

Yield: 67% of theory.

EXAMPLE 13

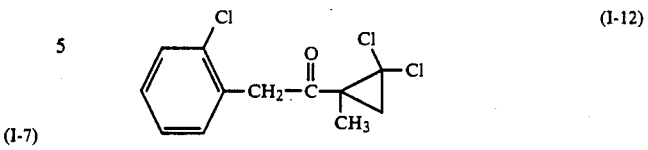
(I-12)

Yield: 91% of theory.
¹H-NMR(200 MHz, CDCl₃) : δ=1.35(d,J≃7 Hz;1H), 1.73 (s;3H), 2.29(d,J≃7 Hz;1H), 3.9(d,J≃17.5 Hz;1H), 4.3 (d,J≃17.5 Hz;1H), 7.1-7.4(m;4H) ppm.

EXAMPLE 14

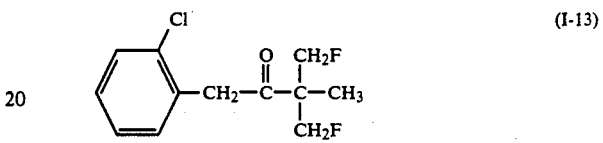
(I-13)

Yield: 93% of theory.
¹H-NMR(200 MHz, CDCl₃) : δ=1.3(t,J≃1Hz;3H), 3.99 (d,J≃20 Hz;1H), 4.01(d,J≃20 Hz;1H), 4.6 (ddd,J₁≃47 Hz, J₂≃9.5 Hz, J₃≃2 Hz;4H), 7.1-7.4(m;4H) ppm.

EXAMPLE 15

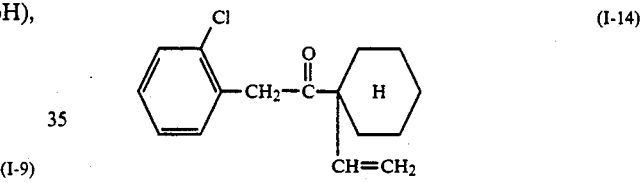
(I-14)

Yield: 70% of theory.
¹H-NMR(200 MHz, CDCl₃) : δ=1.3-2.2(m;10H), 3.90 (d,J≃21 Hz;1H), 3.92(d,J≃21 Hz;1H), 5.2 (dd,J₁≃17 Hz, J₂≃1Hz;1H), 5.3(dd,J₁≃11 Hz, J₂≃1 Hz;1H), 5.8(dd,J₁≃17 Hz, J₂≃11Hz;1H), 7.0-7.4 (m;4H) ppm.

EXAMPLE 16

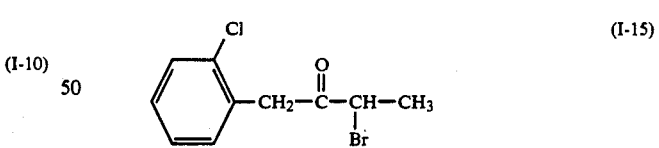
(I-15)

Yield: 86% of theory.
¹H-NMR (200 MHz, CDCl₃) : δ=1.75(d,J≃7 Hz;3H), 4.13 (s;2H), 4.5(q,J≃7 Hz;1H), 7.2-7.4(m;4H) ppm.

EXAMPLE 17

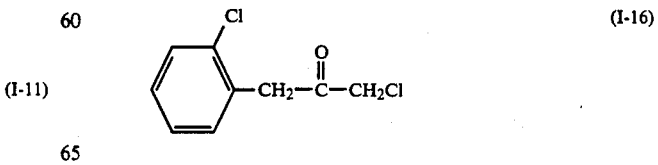
(I-16)

Yield: 90% of theory.
¹H-NMR(200 MHz, CDCl₃) : δ=3.99(s;2H), 4.18(s;2H), 7.2-7.5(m;4H) ppm.

EXAMPLE 18

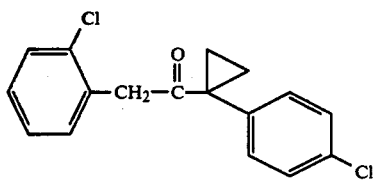
(I-17)

Yield: 95% of theory.

$^1$H-NMR (200 MHz, CDCl$_3$) : δ=1.15–1.25 (m; 2H), 1.65–1.75 (m, 2H), 3.68 (s; 2H), 7.0–7.4 (m; 8H) ppm.

EXAMPLE 19

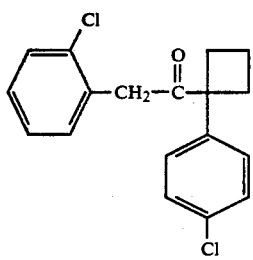
(I-18)

Yield: 80% of theory.

$^1$H-NMR (200 MHz, CDCl$_3$) : δ=1.8–2.05 (m; 2H), 2.3–2.55 (m; 2H), 2.8–3.0 (m; 2H), 3.63 (s; 2H), 6.9–7.4 (m; 8H) ppm.

EXAMPLE 20

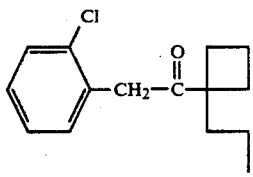
(I-19)

Yield: 88% of theory.

$^1$H-NMR (200 MHz, CDCl$_3$) : δ=0.8–1.0 (t, 3H), 1.1–1.3 (m; 2H), 1.7–2.0 (m; 6H), 2.35–2.6 (m; 2H), 3.81 (s; 2H), 7.1–7.4 (m; 4H) ppm.

EXAMPLE 21

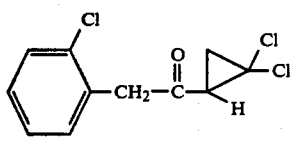
(I-20)

Yield: 89% of theory.

$^1$H-NMR (200 MHz, CDCl$_3$): δ=1.8 (dd, J$_1$≈9 Hz, J$_2$≈6 Hz; 1H), 2.15 (dd, J$_1$≈7.5 Hz, J$_2$≈6 Hz, 1H), 2.8 dd, J$_1$≈9 Hz, J$_1$≈7.5 Hz, 1H), 4.05 (s, 2H), 7.2–7.5 (m, 4H) ppm.

EXAMPLE 22

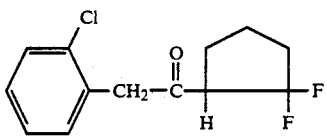
(I-21)

Yield: 76% of theory.

$^1$H-NMR (200 MHz, CDCl$_3$) : δ=1.6–2.4 (m; 6H), 3.25–3.5 (m; 1H), 3.97 (d, J≈16 Hz; 1H), 4.03 (d, J≈16 Hz; 1 H), 7.1–7.5 (m; 4H) ppm.

EXAMPLE 23

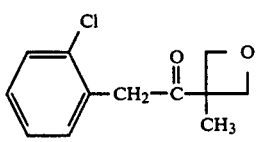
(I-22)

Yield: 73% of theory.

$^1$H-NMR (270 MHz, CDCl$_3$): δ=1.45 (s; 3H), 3.85 (s; 4H), 4.06 (s; 2H). 7.0–7.4 (m; 5H) ppm.

EXAMPLE 24

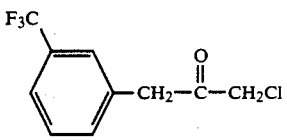
(I-23)

Yield: 80% of theory.

$^1$H-NMR (200 MHz, CDCl$_3$): δ=3.95 (s; 2H), 4.12 (s; 2H), 7.35–7.6(m;4H)ppm.

Melting point: 42° C.

EXAMPLE 25

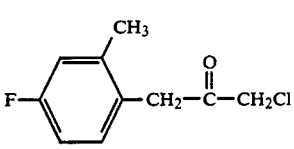
(I-24)

Yield: 55% of theory.

$^1$H-NMR (200 MHz, CDCl$_3$): δ=2.20 (s; 3H), 3.84 (s; 2H), 4.08 (s; 2H), 6.8–7.15 (m; 3H) ppm.

Boiling point: 99°–103° C./1 mbar.

EXAMPLE 26

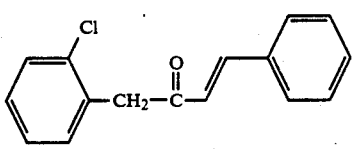
(I-25)

Yield: 40% of theory.

$^1$H-NMR (200 MHz, CDCl$_3$): δ=4.08 (s; 2H), 6.78 (d,J≈16 Hz; 1H), 7.2–7.6 (m;9H), 7.65 (d,J≈16 Hz; 1H) ppm.

EXAMPLE 27

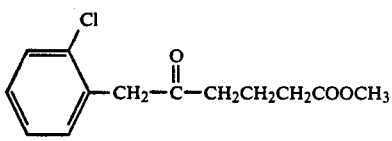
(I-26)

Yield: 80% of theory.

$^1$H-NMR (200 MHz, CDCl$_3$): δ=1.8-2.0 (m; 2H), 2,33 (t, J≃7 Hz; 2H), 2.55 (t,J≃7 Hz; 2H), 3.63 (s; 3H), 3.80 (s; 2H), 7.1-7.4 (m; 4H) ppm.

EXAMPLE 28

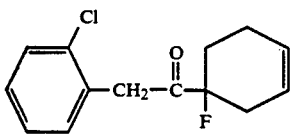
(I-27)

Yield: 80% of theory.

$^1$H-NMR (200 MHz, CDCl$_3$): δ=1.65-2.8 (m; 6H), 4.0-4.3 (m; 2H), 5.5-5.9 (m; 2H), 7.1-7.5 (m; 4H) ppm.

EXAMPLE 29

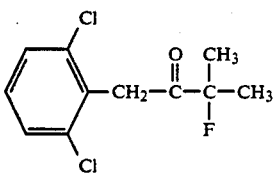
(I-28)

Yield: 59% of theory.

$^1$H-NMR (200 MHz, CDCl$_3$): δ=1.56 (d, J≃21 Hz; 6H), 4,35 (m; 2H), 7.1-7.35 (m; 3H) ppm.

EXAMPLE 30

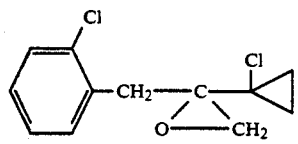
(IX-1)

82.2 g (0.64 mol) of trimethylsulphoxonium chloride are added in portions to a mixture of 134 g (0.585 mol) of 2-chlorobenzyl 1-chlorocyclopropyl ketone and 35.5 g (0.64 mol) of potassium hydroxide powder in 700 ml of absolute n-butanol at room temperature, while stirring. When the addition has ended, the reaction mixture is stirred at 35° C. for a further 3 hours and then stirred into 500 ml of water. The organic phase is separated off, washed once with 500 ml of water and concentrated under reduced pressure, and the residue which remains is distilled in vacuo. 134.6 g of a product which consists of 2-(2-chlorobenzyl)-2-(1-chlorocyclopropyl)-oxirane to the extent of 92.6% and has a boiling point of 88°-90° C. under a pressure of 0.2 mbar are obtained in this manner. The yield is accordingly calculated as 87.7% of theory.

EXAMPLE 31

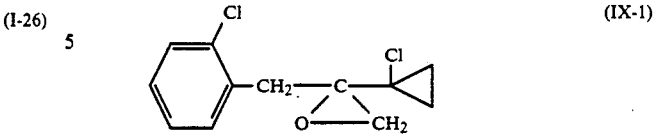
(IX-1)

507 g (5.7 mol) of 45% strength by weight aqueous sodium hydroxide solution are added dropwise to a suspension of 171.0 g (0.75 mol) of 2-chlorobenzyl 1-chlorocyclopropyl ketone and 104.0 g (0 81 mol) of trimethylsulphoxonium chloride in 1000 ml of toluene at 20° C., while stirring. During this procedure, the temperature of the reaction mixture rises up to 32° C. When the addition has ended, the reaction mixture is stirred at 30° C. for a further 4 hours, and 600 ml of water are then added, while cooling. The organic phase is separated off and the aqueous phase is extracted twice more with toluene. After drying over magnesium sulphate, the combined organic phases are concentrated under reduced pressure. 175.6 g of an oily product which consists of 2-(2-chlorobenzyl)-2-(1-chloro-cyclopropyl) -oxirane to the extent of 90.5% are obtained in this manner. The yield is accordingly calculated as 87.3% of theory.

COMPARISON EXAMPLE 1

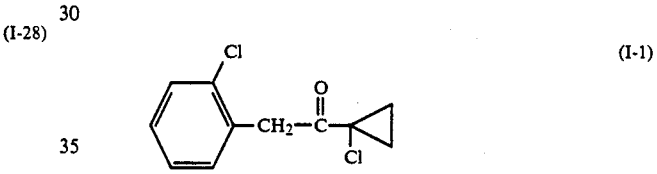
(I-1)

A mixture of 2.6 g (40 mmol) of zinc dust (particle size 325 mesh), 3.2 g (20 mmol) of 2-chlorobenzyl chloride and 25 ml of dry tetrahydrofuran is heated under reflux under a nitrogen atmosphere for 1.5 hours. 2.8 g (20 mmol) of 1-chlorocyclopropane-carbonyl chloride and 7.3 mg (0.05 mol %) of bis(triphenylphosphine)-palladium(II) chloride are then added to the reaction mixture and the mixture is heated under reflux under a nitrogen atmosphere for 2 hours. It is ascertained by analysis by gas chromatography that 2-chlorobenzyl 1-chlorocyclopropyl ketone has formed in a yield of 50% of theory.

COMPARISON EXAMPLE 2

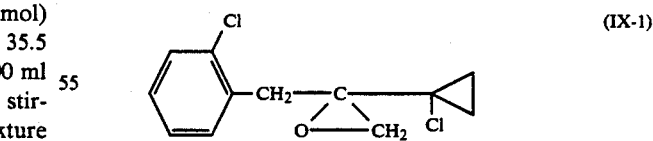
(IX-1)

8.7 g (0.078 mol) of potassium tert.-butylate are added to a suspension of 17.2 g (0.078 mol) of trimethylsulphoxonium iodide in 70 ml of dimethylsulphoxide at room temperature and the mixture is stirred at room temperature for 30 minutes. 15 g (0.066 mol) of 2-chlorobenzyl 1-chlorocyclopropyl ketone are then added. When the addition has ended, the reaction mixture is stirred at 40° C. for 4 hours and, after cooling, is then poured onto water. The mixture formed is extracted several times with methylene chloride. The combined organic phases are washed with water and, after drying over magnesium sulphate, are concentrated under reduced pressure. 16.6 g of an oily product which consists of 2-(2-chlorobenzyl)-2-(1-chloro-cyclopropyl)-oxirane to the extent of 44% are obtained in this manner. The yield is accordingly calculated as 45.5% of theory.

COMPARISON EXAMPLE 3

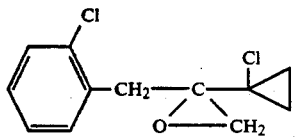 (IX-1)

11.5 g (0.052 mol) of trimethylsulphoxonium iodide are added in proportions to a mixture of 10.0 g (0.044 mol) of 2-chlorobenzyl-1-chloro-cyclopropyl ketone and 2.9 g (0.052 mol) of potassium hydroxide powder in 45 ml of absolute tert.-butanol at room temperature, while stirring. When the addition has ended, the reaction mixture is stirred at 40° C. for a further 16 hours and then stirred into 100 ml of water. The mixture is extracted with 100 ml of methylene chloride, the organic phase is separated off, washed once with 60 ml of water and concentrated under reduced pressure, and the residue which remains is distilled in vacuo. 9 g of a product which consists of 2-(2-chlorobenzyl)-2-(1-chlorocyclopropyl)-oxirane to the extent of 15% are obtained in this manner. The yield is accordingly calculated as 13% of theory.

COMPARISON EXAMPLE 4

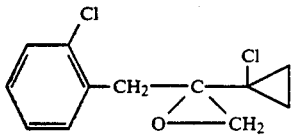 (IX-1)

4.2 g (0.078 mol) of sodium methylate are added to a solution of 13.0 g (0.069 mol) of trimethylsulphoxonium methyl-sulphate in 53 ml of acetonitrile at 20° C., while stirring. When the addition has ended, the mixture is stirred at 20° C. for a further 30 minutes, and 10 g (0.044 mol) of 2-chlorobenzyl-1-chlorocyclopropyl ketone are then added. The mixture is stirred at 20 to 30° C. for 16 hours and then diluted with water. The mixture formed is extracted with methylene chloride. The combined organic phases are washed with water, dried over magnesium sulphate and concentrated under reduced pressure. 7.5 g of an oily product which, according to analysis by gas chromatography, consists of 2-chlorobenzyl-1-chlorgcyclopropyl ketone to the extent of 38% and of 2-(2-chlorobenzyl)-2-(1-chlorocyclopropyl)-oxiranetothe extent of 3.6% are obtained in this manner. The yield is accordingly calculated as 2.5% of theory.

COMPARISON EXAMPLE 5

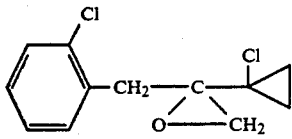 (IX-1)

8.9 g (0.079 mol) of potassium tert.-butylate are added in portions to a suspension of 17.2 g (0.11 mol) of trimethylsulphonium bromide in 70 ml of dimethylsulphoxide at 20° C., while stirring. When the addition has ended, the mixture is stirred at 20° C. for a further 20 minutes, and 15 g (0.0655 mol) of 2-chlorobenzyl-1-chlorocyclopropyl ketone are then added. The mixture is stirred at 40° C. for 4 hours and then at 20° C. for a further 16 hours, and is subsequently diluted with water. The mixture formed is extracted several times with methylene chloride. The combined organic phases are washed with water, dried over magnesium sulphate and concentrated under reduced pressure. 15.5 g of an oily product which, according to analysis by gas chromatography, consists of 2-chlorobenzyl-1-chlorocyclopropyl ketone to the extent of 77% and of 2-(2-chlorobenzyl)-2-(1-chlorocyclopropyl)-oxirane to the extent of 5% are obtained in this manner. The yield is accordingly calculated as 4.9% of theory.

COMPARISON EXAMPLE 6

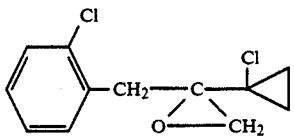 (IX-1)

7.5 g (0.13 mol) of potassium hydroxide powder are added to a mixture of 10 g (0.044 mol) of 2 chlorobenzyl 1-chlorocyclopropyl ketone, 50 mg of oleic acid polyglycolether and 0.1 ml of methanol in 11 ml of toluene at 20° C., while stirring. The mixture is then heated to 40° C., and a solution of 6.6 g (0.059 mol) of trimethylsulphonium chloride in a mixture of 1.5 ml of water and 0.2 ml of diethylene glycol is added dropwise, while stirring. The reaction mixture is stirred at 40° C. for 16 hours and then diluted with water. The mixture formed is extracted with toluene. The combined organic phases are concentrated under reduced pressure. 11.3 g of an oily product which consists of 2-(2-chlorobenzyl)-2-(1-chloro-cyclopropyl)-oxirane to the extent of 12% are obtained in this manner, the yield is accordingly calculated as 13% of theory.

USE EXAMPLE

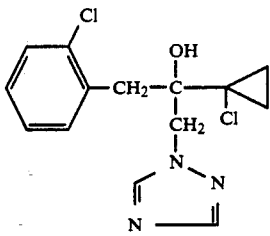 (V-1)

A solution of 2.84 g of 2-(2-chlorophenyl)-2-(1-chlorocyclopropyl)-oxirane in 3 ml of dry dimethylformamide is added dropwise to a mixture of 2.2 g of 1,2,4-triazole and 0.23 g of potassium tert.-butylate in 10 ml of dry dimethylformamide under a nitrogen atmosphere at 80° C., while stirring. When the addition has ended, the reaction mixture is heated at 80° C. for a further 8 hours and then concentrated under reduced pressure. The residue which remains is dissolved in ethyl acetate. The solution formed by this operation is extracted by shaking with water and the extract is dried and concentrated under reduced pressure. The residue which remains is chromatographed over a silica gel column using methylene chloride as the mobile phase. Evaporation of the eluate gives 1.77 g of 3-(2-chlorophenyl)-2-(1-chloro-cyclopropyl)-1-(1,2,4-triazol-1-yl)-propan-2-ol in the form of a solid substance of melting point 107° C.

It will be understood that the specification and examples are illustrative but not limitative of the present invention and that other embodiments within the spirit and scope of the invention will suggest themselves to those skilled in the art.

We claim:

1. A process for the preparation of 2-(2-chlorobenzyl)-2-(1-chloro-cyclopropyl)-oxirane of the formula

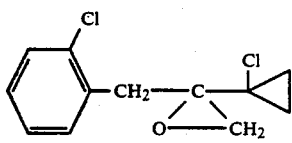 (IX-1)

which comprises reacting 2-chlorobenzyl 1-cyclopropyl ketone of the formula

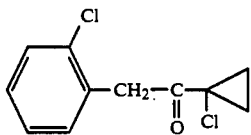 (I-1)

with trimethylsulphoxonium chloride of the formula $(CH_3)_3 {\oplus} SO\ Cl^{\ominus}$ (XI)

either
γ) in the presence of an alcohol and in the presence of an alkali metal hydroxide or an alkali metal alcoholate,
or
δ) in the presence of toluene or xylene and in the presence of aqueous sodium hydroxide solution or potassium hydroxide solution
at a temperature between 10° C. and 60° C.

* * * * *